(12) United States Patent
Yeretsian

(10) Patent No.: US 6,688,312 B2
(45) Date of Patent: Feb. 10, 2004

(54) CLOSED BLOODLESS HEMORRHOIDECTOMY METHOD

(76) Inventor: Sarkis Yeretsian, 205 Leger, Laval, Quebec (CA), H7G 3T1

(*) Notice: Subject to any disclaimer, the term of this patent is extended or adjusted under 35 U.S.C. 154(b) by 10 days.

(21) Appl. No.: 10/152,563

(22) Filed: May 23, 2002

(65) Prior Publication Data

US 2003/0005939 A1 Jan. 9, 2003

Related U.S. Application Data

(60) Provisional application No. 60/292,631, filed on May 23, 2001.

(51) Int. Cl.⁷ ............................................. A61B 19/00
(52) U.S. Cl. ...................................... 128/898; 606/205
(58) Field of Search .................. 128/898; 606/110–111, 606/205–211

Primary Examiner—Corrine McDermott
Assistant Examiner—Thomas Barrett
(74) Attorney, Agent, or Firm—Christian Cawthorn; Ogilvy Renault

(57) ABSTRACT

The present invention relates to a new cosmetic method for removing hemorrhoids. The method comprises sequentially the steps of 1) Isolating a hemorrhoidal mass from a patient with a curved forceps applied at the perianal skin outside the mucocutaneous junction, and eversion of the internal and external hemorrhoidal mass. 2) Application of another curved forceps at the base of the internal hemorrhoid, and suturing under the forceps with 20 catgut (securing hemostasis), then amputation of the internal hemorrhoid with a knife. 3) Leaving the first forceps in place, application of the second forceps at the base of the external hemorrhoid, suturing as above, amputation of the external hemorrhoid, and removal of the forceps. 4) This procedure is repeated for the remaining hemorrhoids.

5 Claims, 6 Drawing Sheets

CLOSED BLOODLESS HEMORRHOIDECTOMY METHOD

CROSS REFERENCE TO RELATED APPLICATIONS

This application claims priority under 35 USC §119(e) of U.S. application Ser. No. 60/292,631 filed May 23, 2001.

TECHNICAL FIELD

The present invention relates to a new surgical procedure for hemorrhoids.

BACKGROUND OF THE INVENTION

Hemorrhoids are essentially normal parts of human anatomy and it is considered a disease of western civilization. It is extremely rare in rural Africa due to, In principle, high fiber diet consumption. Contributing factors include heredity, anatomical features, nutrition, exercise, occupation, psychological problems, senility, endocrine changes, food and drugs, straining, constipation, diarrhea, and inflammatory bowel diseases and intestinal neoplasm.

It is difficult to figure out the exact incidence and prevalence of hemorrhoids because primary care physicians will screen and treat patients who may or may not have hemorrhoids but have hemorrhoidal symptoms. Many patients with hemorrhoids choose not to come for consultation and will treat themselves with ointments, creams, lotion or application of cold or heat. In 1990, Johnson and Sonnenberg studied the prevalence of hemorrhoids and chronic constipation and estimated that ten million people in the United States complained of hemorrhoids, a prevalence rate of 4.4%.

The real cause of hemorrhoids is not known. There is no single theory that could explain the occurrence and the frequency of hemorrhoids. It depends, most probably, on many factors. The very attractive theory of "vascular cushions" of Thomson described in 1975 does not explain the occurrence of hemorrhoids in young mate and female between 20–30 of age where there is no deterioration or weakening of supporting and anchoring tissue of hemorrhoids. In youngster, the occurrence of sudden, localized in one portion, thrombosed hemorrhoids is more frequent. On the other hand, hemorrhoids are not that frequent in old population where aging could be considered a more plausible factor. In his theory, Thomson propose that normal hemorrhoidal tissue represent discrete masses of thickened submucosa, which slide with straining efforts of defecation. These vascular cushions become engorged with blood and serve some sort of function in the canal anal, preventing the escape of fluid, gas, or solid fecal material. With the passage of time, anatomic structures supporting the muscularis submucosae weaken and lead to slippage or prolapsation with subsequent symptoms such as bleeding, engorgement, burning and discomfort.

There are three main cushions in the anal region; the left lateral, the right anterior and the right posterior one. The anal cushions receive their blood supply from the terminal branches of the superior hemorrhoidal artery (superior rectal artery) and to a lesser extent, from branches of the middle hemorrhoidal arteries. These branches communicate with one another and with branches of inferior hemorrhoidal arteries, which supply the lower portion of the anal canal. The superior, middle and inferior hemorrhoidal veins, which drain blood from the tissues from the anal canal, correspond to each of hemorrhoidal arteries.

Haas et al have noted microscopically, deterioration of supportive tissue by the third decade of life.

Stelzner et al thought that swollen tissue of anorectum might represent "a corpus cavernosum" as they demonstrated numerous arteriovenous communications in the anal region.

Constipation is incriminated as a cause of hemorrhoids; however, only less than 20% of patients operated on for hemorrhoids complain of constipation. Diarrhea is known to cause hemorrhoids to flare. Gibbons et al. investigated chronic constipation, bowel habits, and pressure profiles, and anal compliance and found that symptomatic hemorrhoids were associated with significantly longer anal pressure zones as well as greater maximum resting pressure at all levels of anal distention.

Hyperactive sphincter found before hemorrhoidectomy returns to normal after surgery, but the relationship is not that clear.

Hemorrhoids are classified by their location (external, internal, or mixed) or by degree (first, second, third, and forth).

External hemorrhoids arise from the inferior hemorrhoidal plexus and are covered by anoderm, which is modified skin epithelium, bearing no skin appendages. They are situated below the dentate line. Distribution is most commonly the right anterior, right posterior, and left lateral position.

Internal hemorrhoids arise above dentate line and covered by transitional or columnar epithelium. They may prolapse and may be reducible or may be irreducible. They arise from superior hemorrhoidal plexus.

Mixed hemorrhoids (external, internal) may be prolapsed, irreducible, thrombosed, or ulcerated. They arise from superior and inferior hemorrhoidal plexi and their anastomotic connections.

First-degree hemorrhoids, veins of anal canal are increased in number and size and may bleed at the time of defecation. They do not prolapse but project into the lumen.

Second-degree hemorrhoids present to the outside during defecation but return within the anal canal spontaneously.

Third-degree hemorrhoids (internal, external) protrude outside the canal anal and require manual reduction.

Forth-degree hemorrhoids are irreducible and remain in the prolapsed position at all time.

An accurate diagnosis can be made by taking a careful history. Since bleeding is the most presenting symptom, questions should be asked about not only the amount of blood but also the color, whether the bleeding is painful, mixed with stool. Questions about bowel habits, abdominal pain, sensation of burning, incomplete emptying with bowel movements, fullness, bulging.

Evaluation include general medical condition, bleeding problems, portal hypertension, chronic constipation, intermittent diarrhea.

Physical examination is directed on the abdomen, the groin area, the genitalia, the appearance of the perineum and the condition of the skin.

The patient is examined in the supine, left lateral, or Jackknife position. Digital rectal examination palpate the most external portion of the anus, the middle canal and the entire canal and anorectal ring is examined. The degree of anal tone is assessed, the relative length, and its spasticity.

Anuscope is the most important method of exposing the entire anal canal to the level of anorectal ring. Rigid sigmoidoscope will discover pathological conditions in the first 20 cm above the anorectal ring. If the history of the patient is suggestive of other abnormalities, the investigation will be completed by a double-contrast barium and colonoscopy.

There is constant evolution in the surgical treatment of hemorrhoids. Modifications on this subject have evolved over time from open to closed method of excisional hemorrhoidectomy. Hippocrates performed most likely an open hemorrhoidectomy 2000 years ago, In the middle Ages, hemorrhoids were most probably treated with mass ligation of the entire internal and external hemorrhoidal complex. Over 2000 years ago the French anatomist Jean Louie Petit recognized the sensitivity of hemorrhoidal epithelium and tried to excise hemorrhoids without denuding the lower anal canal of its mucosa. In 1959, Ferguson and Heaton described the Ferguson technique of closed hemorrhoidectomy since that time, closed hemorrhoidectomy has become widely accepted and practiced. In 1882, Whitehead, a British surgeon, described a circumferential amputation of hemorrhoids. Every surgical treatment of hemorrhoids results in complications that are classified as early or late complication. Complications due to surgical difficulties (Parks hemorrhoidectomy) which is bloody and tedious to perform and complications due to the location of the surgical procedure such as ano-rectum which is a functional anatomical region for stools and gas to be eliminated regularly.

Other forms of therapy are described with variable results: sclerotherapy, forceful anal dilatation, elastic band ligation, infrared coagulation, cryogenic coagulation, and laser hemorrhoidectomy.

It would be highly desirable to be provided with a new and rapid office procedure done under local or loco-regional anesthesia for removing hemorrhoids.

SUMMARY OF THE INVENTION

One aim of the present invention is to provide a new and rapid office procedure done under local or loco-regional anesthesia for removing hemorrhoids In accordance with the present invention there is provided a new surgical procedure for removing hemorrhoids as described herein. More particularly, there is provided a method for removing a hemorrhoidal mass from a patient, said method comprising sequentially the steps of:

a) isolating an hemorrhoidal mass from a patient with a forceps applied at the base of said hemorrhoidal mass, said forceps having a proximal side in contact with the perianal region of the patient and a distal side in contact with the hemorrhoidal mass;

b) suturing on the proximal side of the forceps the tissue of the perianal region along said forceps to cause hemostasis in the hemorrhoidal mass;

c) cutting off from the patient on the distal side of the forceps the hemorrhoidal mass; and d) removing the forceps from the patient.

When suturing in step b), proximal and distal threads are preferably left to control a possible hemorrhage by pulling said threads in opposite direction. Additional forceps may also be placed at the perianal region for exposing the hemorrhoidal mass.

The innovative surgical hemorrhoidectomy of the present invention is very easy to perform. It is an office procedure, done always under local anesthesia, and has almost no complications due to surgical technique itself.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION OF THE PREFERRED EMBODIMENT

The new innovative surgical hemorrhoidectomy described below respects the entire anatomy of the ano-rectum without anal distortion after completion of the intervention. It is practiced without any I-V sedation, it is very economical and practical. It is bloodless, and allows to control the amount of tissue to be excised. It has been used exclusively for hemorrhoids grade 3 and grade 4 as well as for thrombosed, circular, and gangrenous, edematous hemorrhoids. It was used elegantly for rectal mucosal prolapse. The patient leaves the office after the operation on his feet due to lack of I-V sedation.

It should be mentioned before the description of this new technique of hemorrhoidectomy that the procedure is preferably performed with an ordinary curved hemostat (also referred to as crile or forceps) or with a mosquito depending upon the volume of hemorrhoids. Preferably, the curved hemostat has been modified by tailoring the two jaws of the forceps in order to have the same width from proximal to the distal part till the articulation of the forceps. This modification thus allows to have an equal and linear surgical wound after the completion of the operation.

Before beginning the procedure, every step is explained to the patient in order to obtain his or her consent and confidence.

Preparation for operation is minimal. Patient is asked to have bowel movements before coming to the office. The patient is on fasting. Neither laxatives, enema nor antibiotics are used preoperatively or during the procedure.

Figure 1:
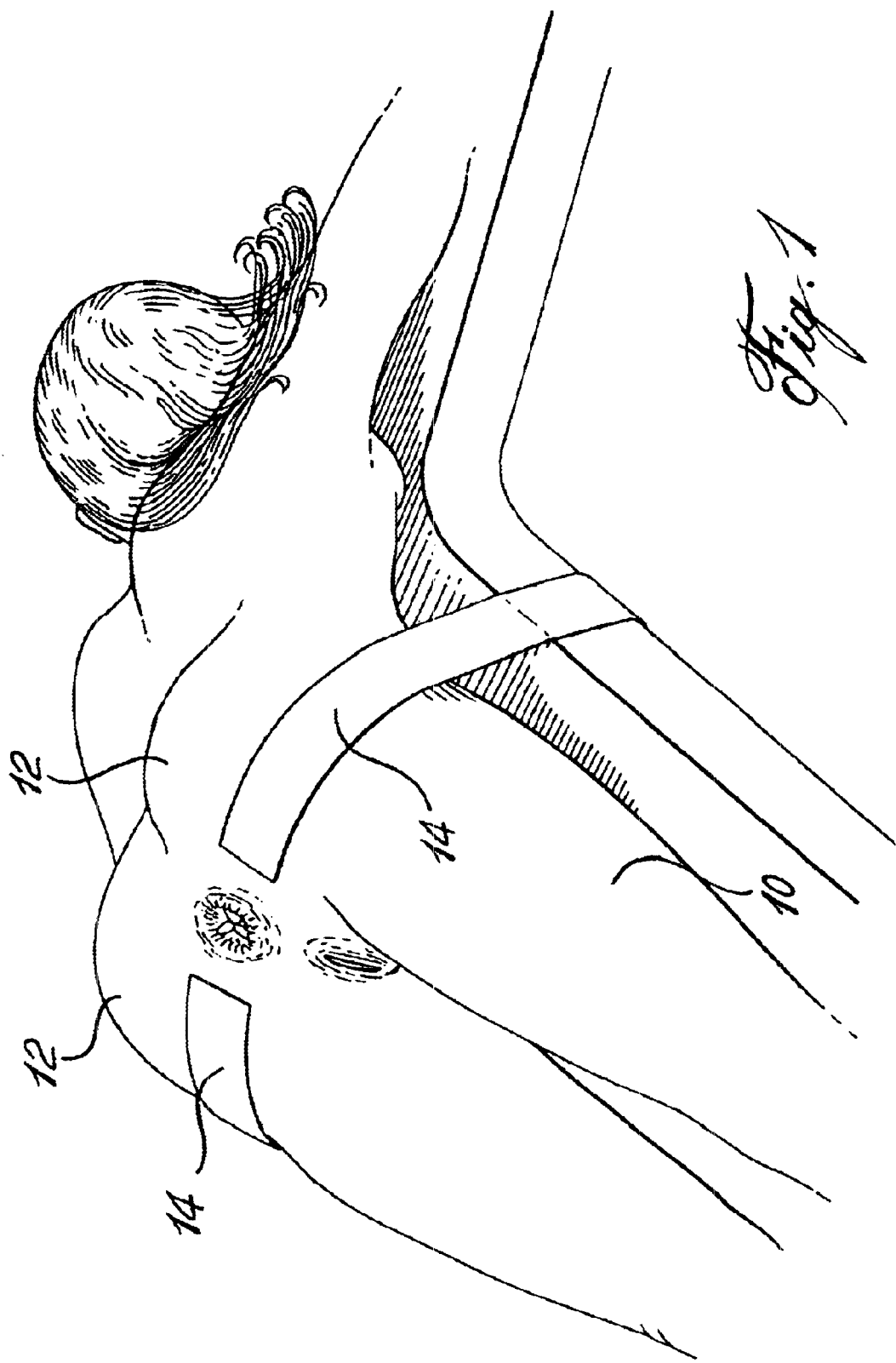
FIG. 1 illustrates a patient in a jackknife position ready for hemorrhoidectomy.

In the operating room, a patient 10 is placed in a jackknife position, (FIG. 1) and the buttocks 12 are retracted with adhesive tape 14 or with the help of an assistant. The operative is cleansed with hibitane solution. The area does not need to be shaved.

Figure 2:
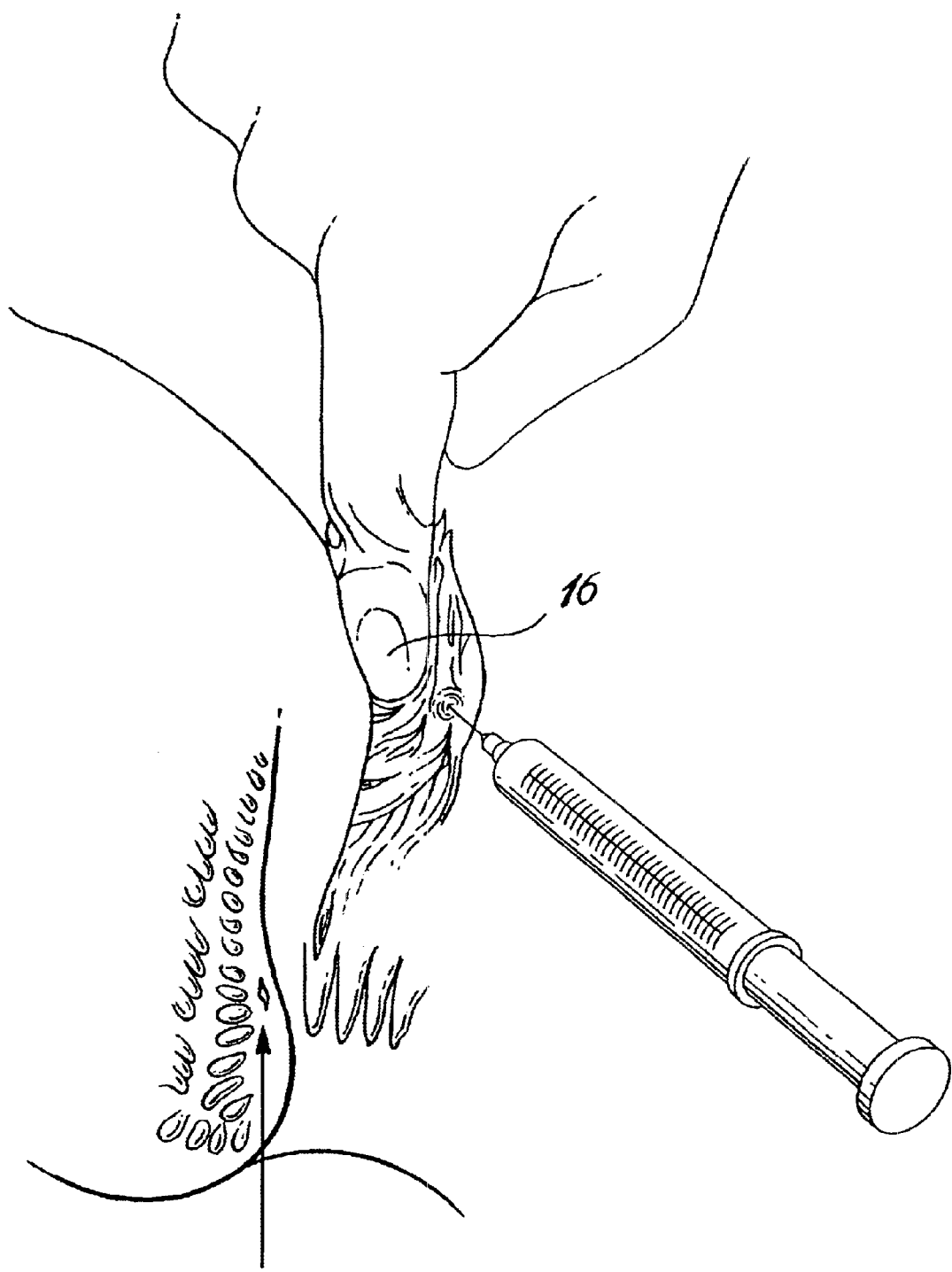
FIG. 2 illustrates a local anesthesia of a patient prior to hemorrhoidectomy.

Local anesthesia such as with xylocaine 1% with or without epinephrine is infiltrated subcutaneously into each hemorrhoidal mass to be removed with No. 30 gauge needle at each side, then the infiltration is extended beneath the mucocutaneous junction and the lining of the lower part of the anal canal (FIG. 2). Further amount of local anesthetic solution 5–7 ml are placed at the four quadrants of the anus after localizing with the index finger 16 the intersphincteric groove. The needle for this purpose is changed for a No. 25 gauge needle to reach the level of anorectal ring at 3,6,9,12 o'clock, Before the infiltration of xylocaine is carried out it is ensured by aspiration that a vessel has not been entered.

After a successful anesthesia, the sphincteric relaxation can easily be seen. A gentle two-finger dilatation of the anal sphincter is performed to allow the anal canal to be opened.

Figure 3:
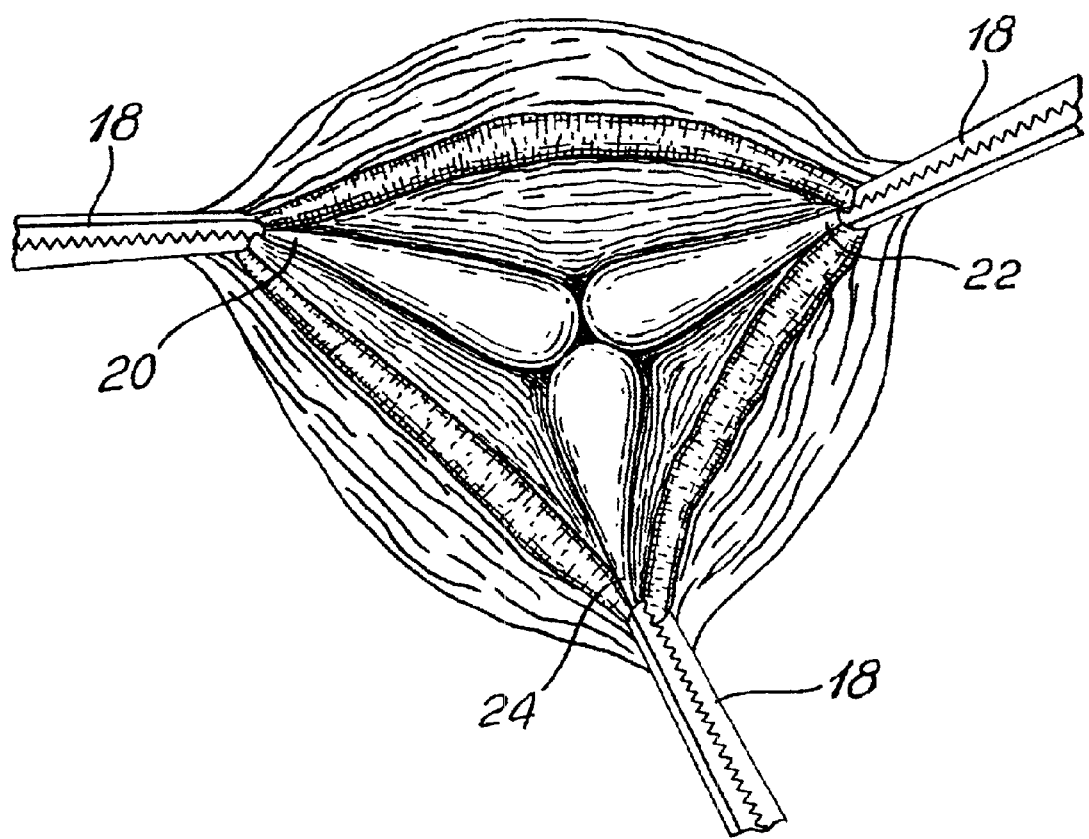
FIG. 3 illustrates the positioning of forceps at the perianal skin according to one embodiment of the present invention for exposing the hemorrhoidal mass to be removed.

In one embodiment of the present invention, forceps 18 are placed at the perianal skin outside the mucocutateous junction opposite each primary hemorrhoidal cushion (left lateral 20, right anterior 22, right posterior 24) (FIG. 3). A gentle traction is exercised on the forceps and an aversion of the hemorrhoidal complex is obtained. No speculum, no retractor is used.

Figure 4:
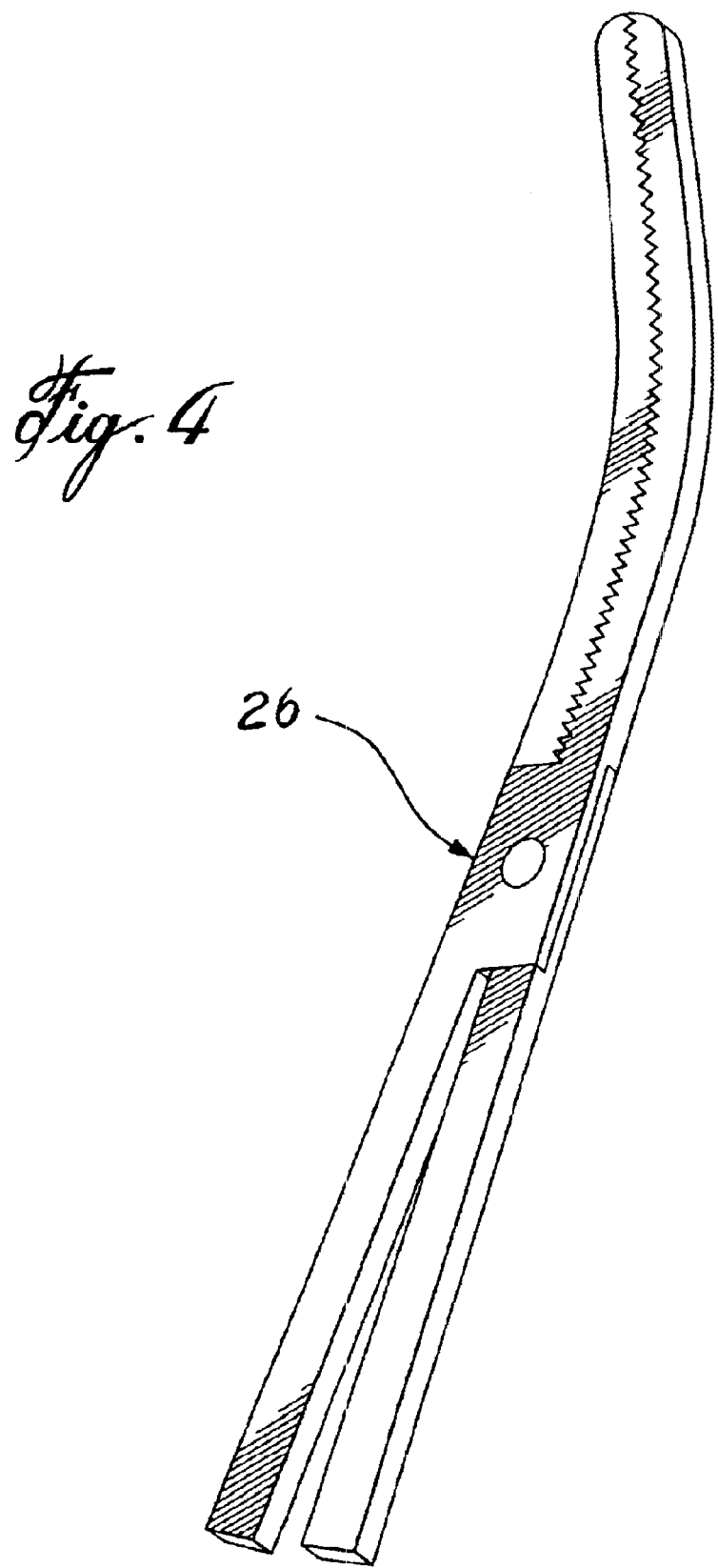
FIG. 4 illustrates the curved crile used according to one embodiment of the present invention.
Figure 5:
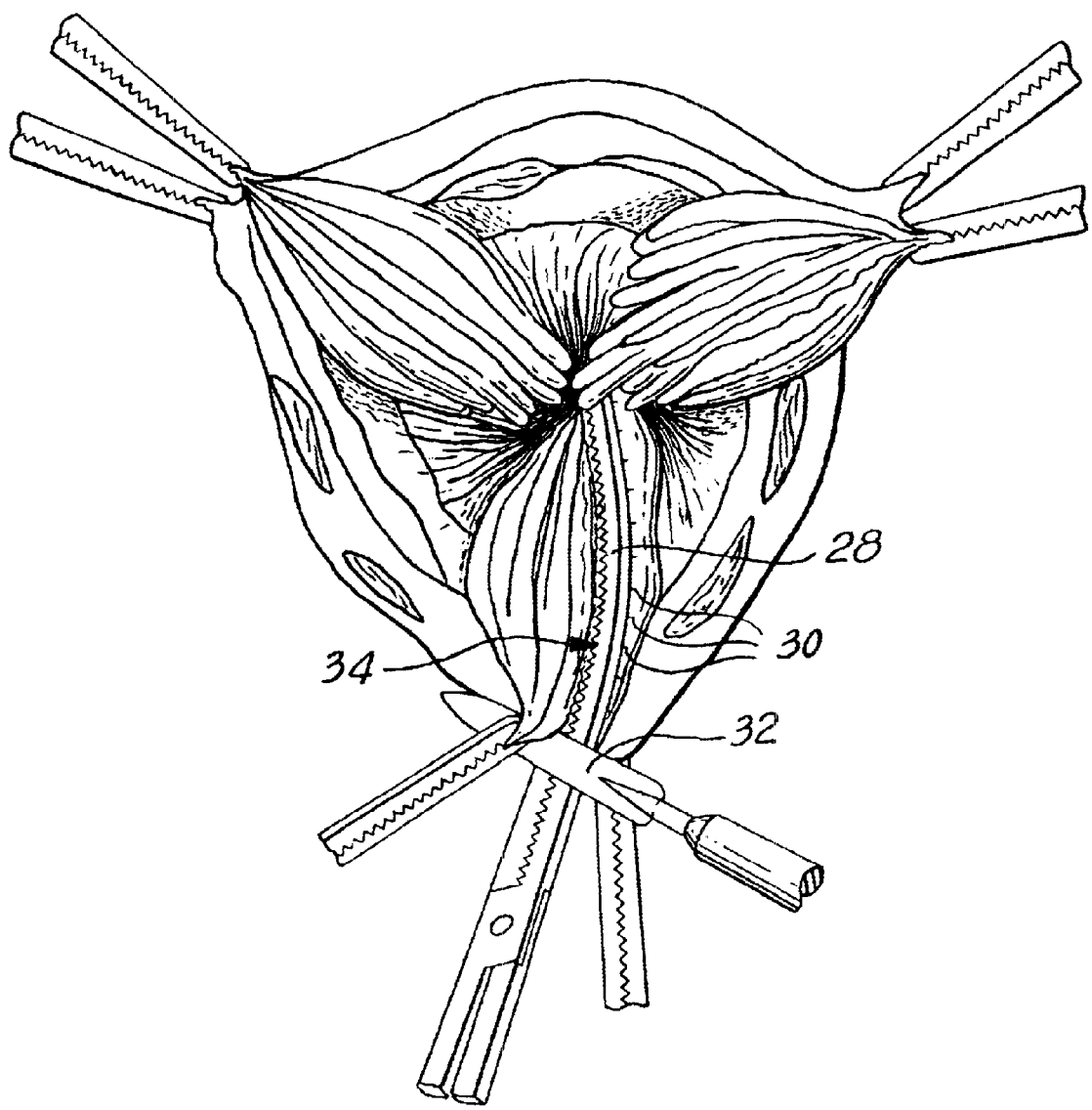
FIG. 5 illustrates mixed internal and external hemorrhoids of a patient about to have an hemorrhoidectomy practiced according to the present invention.

For a mixed internal and external hemorrhoids on the same fine, the modified curved crile 26 (FIG. 4) is applied first, at the base of the internal hemorrhoid 28 (FIG. 5) then with a catgut chromic No. 2 a running suture 30 is passed under the modified crile from the anal canal to the perianal skin, then a knife 32 is applied at the concave aspect 34 of the forceps and an excision of the internal hemorrhoidal mass is performed. Then the modified forceps is applied at the base of the external hemorrhoid by encroaching on the first row of sutures that was used to secure the internal hemorrhoid. The knife is applied at the concave aspect of the modified crile for the excision of the external hemorrhoid resulting in a nice homogeneous linear surgical wound. Hemostasis is secured before excision so there Is no need for electrocautery. A long proximal and distal thread is left in order to control a possible hemorrhage by pulling those threads in opposite direction and placing a figure of eight with the same catgut. This is extremely rare event K the sutures are tightly placed close to each other. The same procedure is applied for the remaining hemorrhoidal complexes.

No perianal v-shaped incision is made, no submucosal sphincteric dissection is made. No electrocautery Is needed: hemostasis is done before excision of hemorrhoids.

After excision of every hemorrhoidal mass, the narrowing of the anal orifice can now be seen, allowing a surgeon to control the amount of tissue to be excised by taking less tissue to avoid an eventual anal stenosis.

Figure 6:
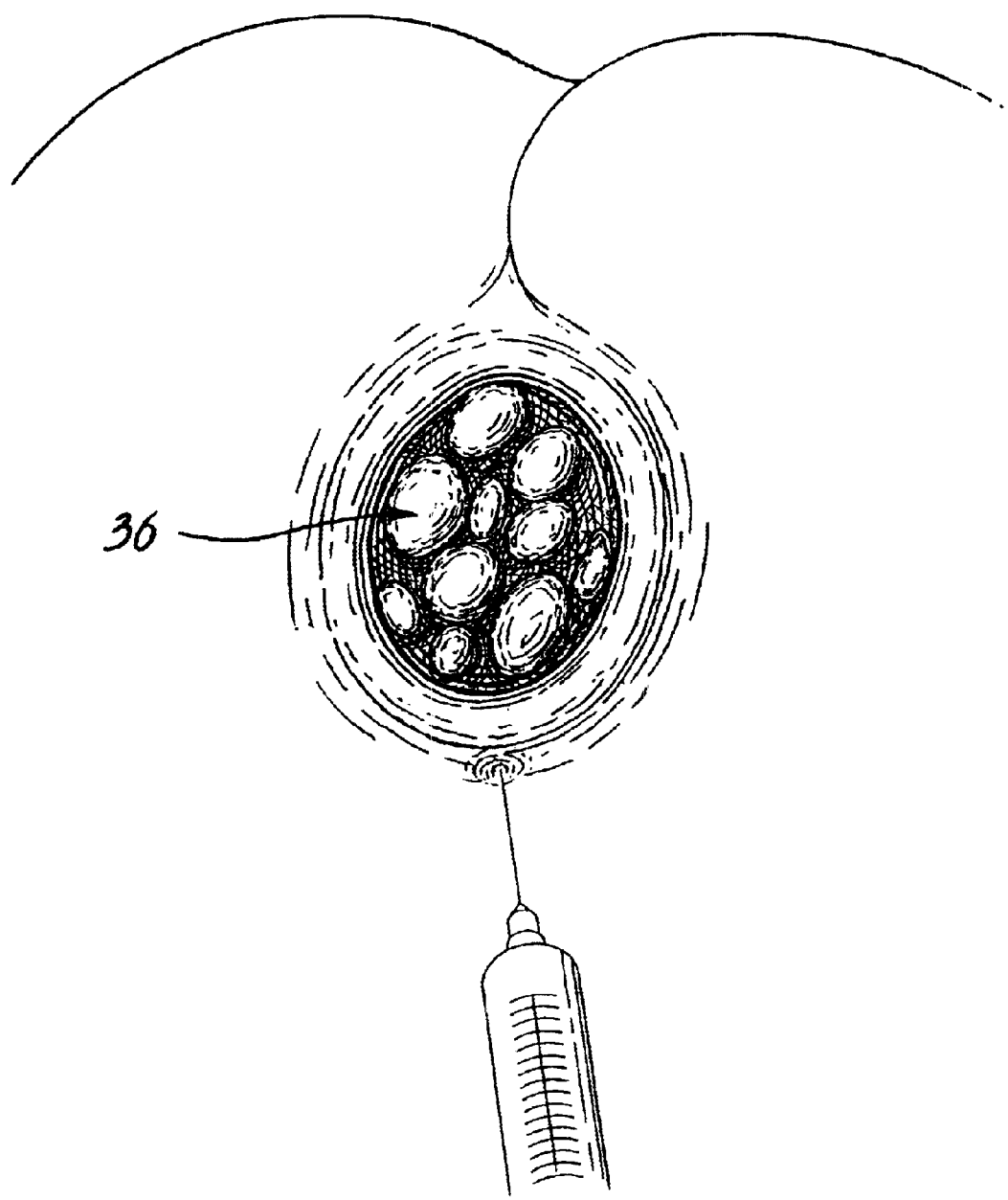
FIG. 6 illustrates circular hemorrhoids of another patient about to have an hemorrhoidectomy practiced according to the present invention.

For circular hemorrhoids 36, (FIG. 6) the most prominent ones are taken off and remaining secondary hemorrhoids are left in place. After 6–8 weeks of observation a band ligation for internal hemorrhoids or remaining rectal mucosal prolapse is done if necessary. Interestingly, rarely such intervention is needed may be by securing the main arteriovenous complex during the previous operation a shrinkage of the secondary hemorrhoids are induced. Some time, it was possible to apply three times the modified hemostat to excise respectively the rectal mucosal prolapse, the internal hemorrhoid, and the external hemorrhoid located in the same quadrant with excellent and very gratifying outcome for the surgeon. The same technique is used for thrombosed and for gangrenous edematous hemorrhoids. In grade 4/4 hemorrhoids (cauliflower) the intensity of the disease is such that it could be very difficult to localize even the anal orifice. By excising rectal mucosal prolapse and the internal hemorrhoid, at the beginning, the surgical field could be less cumbersome and the remaining operation easier. Those cases are encountered specially in woman at the postpartum period. There is no need to combine other form of therapy such as sclerotherapy, infrared coagulation with this particular method, usually the immediate outcome is satisfactory. Some times, rubber band ligation is done only after six weeks of recovery, especially in acute cases with thrombosis and strangulation.

Trimming of redundant skin is done to prevent tag formation. After completion of the operation, the opening of the anal orifice is such that a finger could be Introduced very loosely. A dry gauze is applied externally. The patient may leave the office immediately after the operation on his feet due to lack of I–V sedation and with the usual advices given for these types of surgery.

The method of the present invention can be used for almost all kind of hemorrhoids with excellent results without any case of internal sphincter or rectal muscle inclusion. More particularly, the method of the present invention can be used for hemorrhoid grade 3 and 4, thrombosed hemorrhoids, acute hemorrhoidal diseases specially patients in the post partum period, excision of perianal hematoma, excision of rectal mucosal prolapse, and for other surgical conditions of the anal canal, e.g. fissure, fistula.

One late mild hemorrhage after one week, could be avoided by adding a figure of eight suture over the site of oozing bleeder.

Five cases of anal fissure especially in young patients could be avoided by reducing the amount of tissue excised. In young patients, the perianal skin is very tight. By leaving more tissue, less tension is created on the edges of the wound and the possibility of fissure is reduced. On the contrary, in old patients the perianal skin is very loose. By taking more tissue you may achieve a cosmetic result. Fissure is more often encountered after thrombosed hemorrhoid excision.

The advantages of the method of the present invention over the existing hemorrhoidectomies (Ferguson closed hemorrhoidectomy and St Mark's open hemorrhoidectomy) procedure are numerous. More specifically, one skilled in the art may appreciate these advantages:

- It does not require special skill from one skilled in the art to practice the hemorrhoidectomy of the present invention. Anyone knowing how to suture can use the method of the present invention.
- It can be practiced as an office procedure depending upon the medical condition of the patient.
- It can be done strictly under local anesthesia with xylocaine 1% with or without epinephrine. The effective dosage of xylocaine never exceeds 50 ml.
- It is a bloodless operation except for some bleeding that will occur obviously while suturing.
- Electrocautery is not necessary.
- Allows to control the amount of tissue to be excised and consequently avoids an eventual anal stenosis or fissure.
- No I-V sedation is needed. The patient leaves the office on his feet with usual recommendations.
- Respect meticulously, due to technical aspect of procedure, the anatomy of the anus without any kind of distortion or ectropion formation.
- No single tear of the internal sphincter could be possibly produced because the convex aspect of the modified hemostat is applied on the circular internal sphincter.
- No speculum or retractor is necessary.
- Due to this special technique, an accurate apposition of the wound is realized.
- It could be practiced in all kind of hemorrhoids, even in acute, incapacitating hemorrhoids consisting of thrombosis, prolapse and strangulation of hemorrhoidal tissue involving one or all three primary complexes.
- It could be practiced even on patients suffering from H.B.P.
- Easy to learn and practice; general practitioner could perform the intervention in remote areas.

Very practical and economical.

No long-term complications are observed after six weeks of recovery such as persistent posdefecatory anal pain, fecal urgency or inclusion of rectal muscle as observed following stapled hemorrhoidectomy. (PPH).

Table 1 below provides a comparison between St. Mark's open hemorrhoidectomy, Ferguson closed hemorrhoidectomy, and the method of the present invention. Whitehead hemorrhoidectomy has not been mentioned intentionally because it is not practiced anymore. Table 1 thus clearly shows the differences and advantages of the present invention over the prior art techniques.

TABLE 1

|  | St-Mark's open hemorrhoidectomy | Ferguson's closed hemorrhoidectomy | The method of the present invention |
| --- | --- | --- | --- |
| Indications | Same | Same | Same |
| Preoperative preparation | Same | Same | No enema |
| Position | Same | Same | Jackknife |
| Skin preparation | Same | Same | Same |
| Anesthesia | Same | Same | Strictly local |
| I-V fluid | Yes | Yes | No |
| I-V sedation | Yes or no | Yes or no | No |
| Operation | Dissection - Bloody | Dissection - Bloody | No dissection - Bloodless |
| Speculum, retractor | Yes | Yes | No |
| Prolonged post-defecatory pain | No | No | No |
| Fecal urgency | No | No | No |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for removing a hemorrhoidal mass from a patient, said method comprising sequentially the steps of:
   a) isolating a hemorrhoidal mass from a patient with a forceps applied at the base of said hemorrhoidal mass, said forceps having a proximal side in contact with the perianal region of the patient and a distal side in contact with the hemorrhoidal mass;
   b) suturing on the proximal side of the forceps the tissue of the perianal region along said forceps to cause hemostasis in the hemorrhoidal mass;
   c) cutting off from the patient on the distal side of the forceps the hemorrhoidal mass; and
   d) removing the forceps from the patient.

2. The method of claim 1, wherein when suturing in step b), proximal and distal threads are left to control a possible hemorrhage by pulling said threads in opposite direction.

3. The method of claim 1, wherein before step a), additional forceps are placed at the perianal region for exposing the hemorrhoidal mass.

4. The method of claim 1, wherein before step a), buttocks of the patient are retracted.

5. The method of claim 4, wherein the buttocks of the patient are retracted with tape.

* * * * *